US00PP10481P

United States Patent [19]

Flemer, III

[11] Patent Number: Plant 10,481

[45] Date of Patent: Jul. 7, 1998

[54] CLETHRA ALNIFOLIA PLANT NAMED 'SEPTEMBER BEAUTY'

[75] Inventor: William Flemer, III, Plainsboro Township, Middlesex County, N.J.

[73] Assignee: Treesearch (Partnership), Allentown, N.J.

[21] Appl. No.: 735,639

[22] Filed: Oct. 23, 1996

[51] Int. Cl.[6] ..... A01H 5/00

[52] U.S. Cl. ..... Plt./54.1

[58] Field of Search ..... Plt./54.1

*Primary Examiner*—Howard J. Locker
*Assistant Examiner*—Kent L. Bell

[57] ABSTRACT

A new and distinct Clethra variety characterized by its hardiness and its ability to bloom late in the year coming into fill bloom in September, and having flowers with white petals from pale green buds.

2 Drawing Sheets

BACKGROUND OF THE DISCLOSURE

This invention relates to Clethras and primarily to a Clethra which is a product of crossing a seed parent *Clethra alnifolia* 'rosea' with an unknown pollen parent, in a cultivated area in a nursery located near Plainsboro Twp., N.J.

*Clethra alnifolia* is a very popular shrub because of its pleasant fragrance, attractive inflorescence and ability to thrive in a garden environment, especially in gardens located close to the seashore. It can even be used to form a hedge. The *Clethra alnifolia* 'rosea' generally exhibits flowers with a pink color. Its small flowers are widely evident in late July and do not bloom after about August.

BRIEF SUMMARY OF THE INVENTION

The plant of this application produces flower buds of a pale green with flowers having white petals. Another remarkable aspect of this plant is that it is in bloom in September, long after all other Clethra shrubs have finished blooming. It is a compact grower with thick dark green foliage. Like other Clethras, the leaves turn a clear yellow in the fall, fall colors of the leaves are: Upper surface—Munsell Color Chart Vivid Yellow 5Y 8/12. Lower surface—Munsell Color Chart Brilliant Yellow 5Y 9/9. This new variety greatly extends the blooming period of one of the choicest summer-flowering deciduous shrubs.

I have caused the plant to be asexually reproduced by soft wood cuttings and find that it comes true in successive generations which have been produced over time.

DESCRIPTION OF THE DRAWINGS

This new variety of Clethra is illustrated by the accompanying photographic drawings and depicts the plant by the best possible color representation using color photography.

BOTANICAL DESCRIPTION OF THE PLANT

Figure 1:
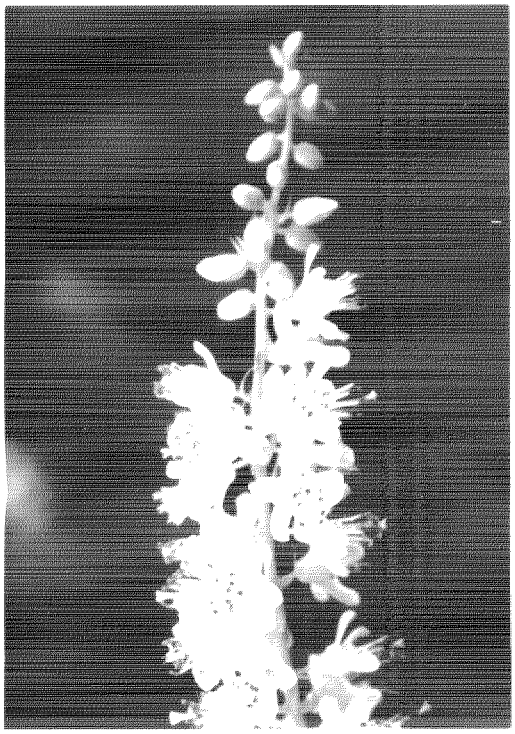
FIG. 1 is a view showing the detail of the flower and the buds.
Figure 2:
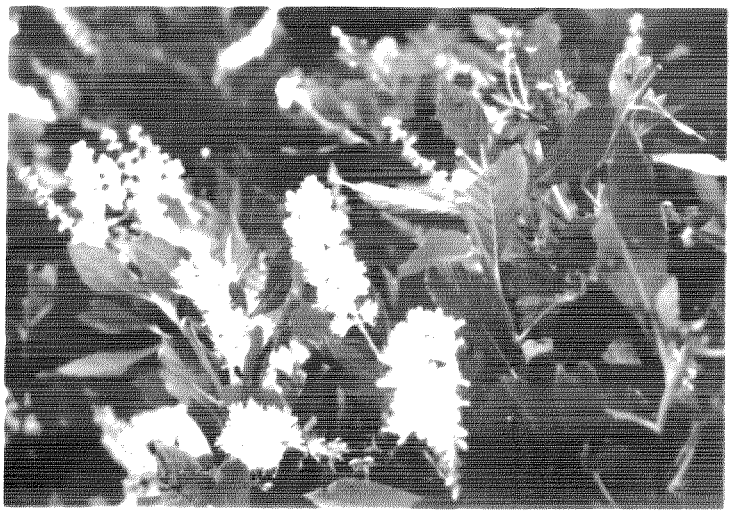
FIG. 2 is a view showing flower clusters and foliage.
Figure 3:
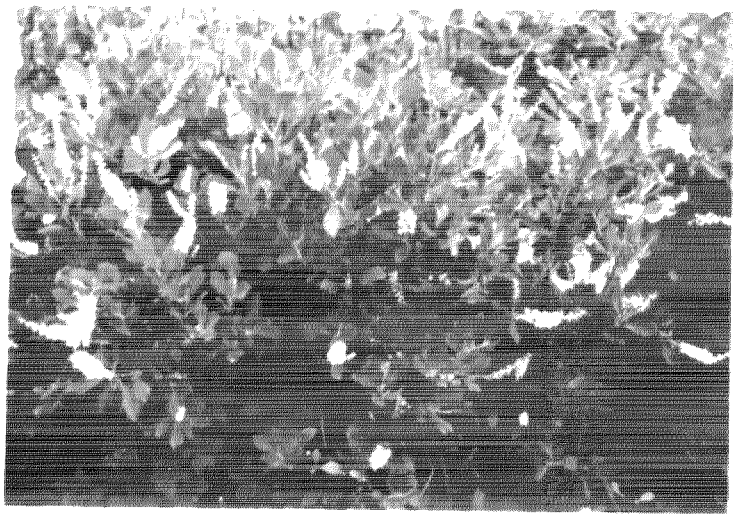
FIG. 3 is a view showing the entire plant.

All color references below are measured against Munsell Limit Color Cascade. Colors are approximate as color depends on horticultural practices such as light level and fertilization rate, among others.

Parentage:

*Seed parent.*—*Clethra alnifolia* 'rosea'. The species of the claimed Clethra plant is *Clethra alnifolia.*

*Pollen parent.*—The pollen was from an unknown plant of the species *Clethra alnifolia,* i.e. open pollinated.

Shrub: Medium, upright, slowly spreading, dense, and hardy. Many stemmed shrub, with dense branches that are slender and smooth.

*Color of branches.*—Strong brown 2.5 YR 4/7. Lenticels not evident. Shrub grows to a size of 2.3 meters tall and 1.4 meters wide.

Leaves:

*Quantity.*—Abundant.

*Length.*—8 to 9 cm.

*Width.*—3½–4 cm.

*Shape.*—Obovate, Acuminate, and thick.

*Color.*—Upper surface—Munsell Color Chart Dark Yellowish Green 2.5G 4/6. Lower surface—Munsell color Chart Strong Yellowish Green 2.5G 5/9.

*Margin.*—Moderately serrate.

*Petiole.*—Short 1 cm long.

*Glands.*—None.

Flower buds: 60 to 70 buds per main panicle, 40 to 50 buds per side panicle. Very hardy, ovate in shape, pale green color, and 0.4 cm in length.

Flowers: Borne in dense terminal panicles, 3 to 4 panicles per twig and richly or intensely fragrant.

*Date of first bloom.*—August 20.

*Date of full bloom*—September 10. Abundant and small in size, average panicle size is 10 cm. long and 2–2½ cm. wide, as measured during blooming season, outdoors in 1993.

Petalage:

*Number of petals.*—5.

*Shape of petals.*—Ovate.

*Size of petals.*—Length 0.6 cm; Width 3 cm.

*Color.*—Pure white, tips of stamens strong orange 2.5 YR 6/12.

Fruits: Dry dehiscent capsules, not significant.

I claim:

1. A new and distinct variety of Clethra plant as illustrated and described herein, characterized particularly as to novelty by its hardiness and its ability to bloom late in the year coming into full bloom in September, and having flowers with white petals from pale green buds.

* * * * *